(12) United States Patent
Kawaguchi

(10) Patent No.: US 6,477,405 B2
(45) Date of Patent: Nov. 5, 2002

(54) HEART-SOUND DETECTING APPARATUS, SYSTEM FOR MEASURING PRE-EJECTION PERIOD BY USING HEART-SOUND DETECTING APPARATUS, AND SYSTEM FOR OBTAINING PULSE-WAVE-PROPAGATION-VELOCITY-RELATING INFORMATION BY USING HEART-SOUND DETECTING APPARATUS

(75) Inventor: Keizoh Kawaguchi, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/902,665

(22) Filed: Jul. 12, 2001

(65) Prior Publication Data

US 2002/0001390 A1 Jan. 3, 2002

(51) Int. Cl.[7] .................................................. A61B 5/02
(52) U.S. Cl. ...................................... 600/513; 600/528
(58) Field of Search ................................ 600/513, 514, 600/528

(56) References Cited

U.S. PATENT DOCUMENTS 4,094,308 A    6/1978    Cormier

FOREIGN PATENT DOCUMENTS

EP    0 498 281 A1    8/1992

OTHER PUBLICATIONS

Wood et al., "Time–Frequency Analysis of the First Heart Sound", IEEE Engineering In Medicine And Biology Magazine, IEEE Inc., New York, vol. 14, No. 2, Mar. 1, 1995, pp. 144–151.

Lee et al., "Comparison between Short Time Fourier and Wavelet Transform for Feature Extraction of Heart Sound", Proceedings of the IEEE Region 10 Conference, South Korea, Sep. 1999, pp 1547–1550.

Primary Examiner—Scott M. Getzow
(74) Attorney, Agent, or Firm—Oliff & Berridge, PLC

(57) ABSTRACT

A heart-sound detecting apparatus, including a heart-sound microphone which detects at least one heart sound produced by the heart of a living subject and outputs a heart-sound signal representing the detected heart sound, a time-frequency analyzing device for analyzing, with respect to time and frequency, at least a portion of the heart-sound signal that includes a first heart sound I, and an aortic-valve-opening-timing determining device for determining a timing when the aortic valve of the heart opens, based on a time when a magnitude of the analyzed signal at a frequency higher than a frequency range of a main component present in an initial portion of the first heart-sound I is greater than a prescribed threshold value.

12 Claims, 7 Drawing Sheets

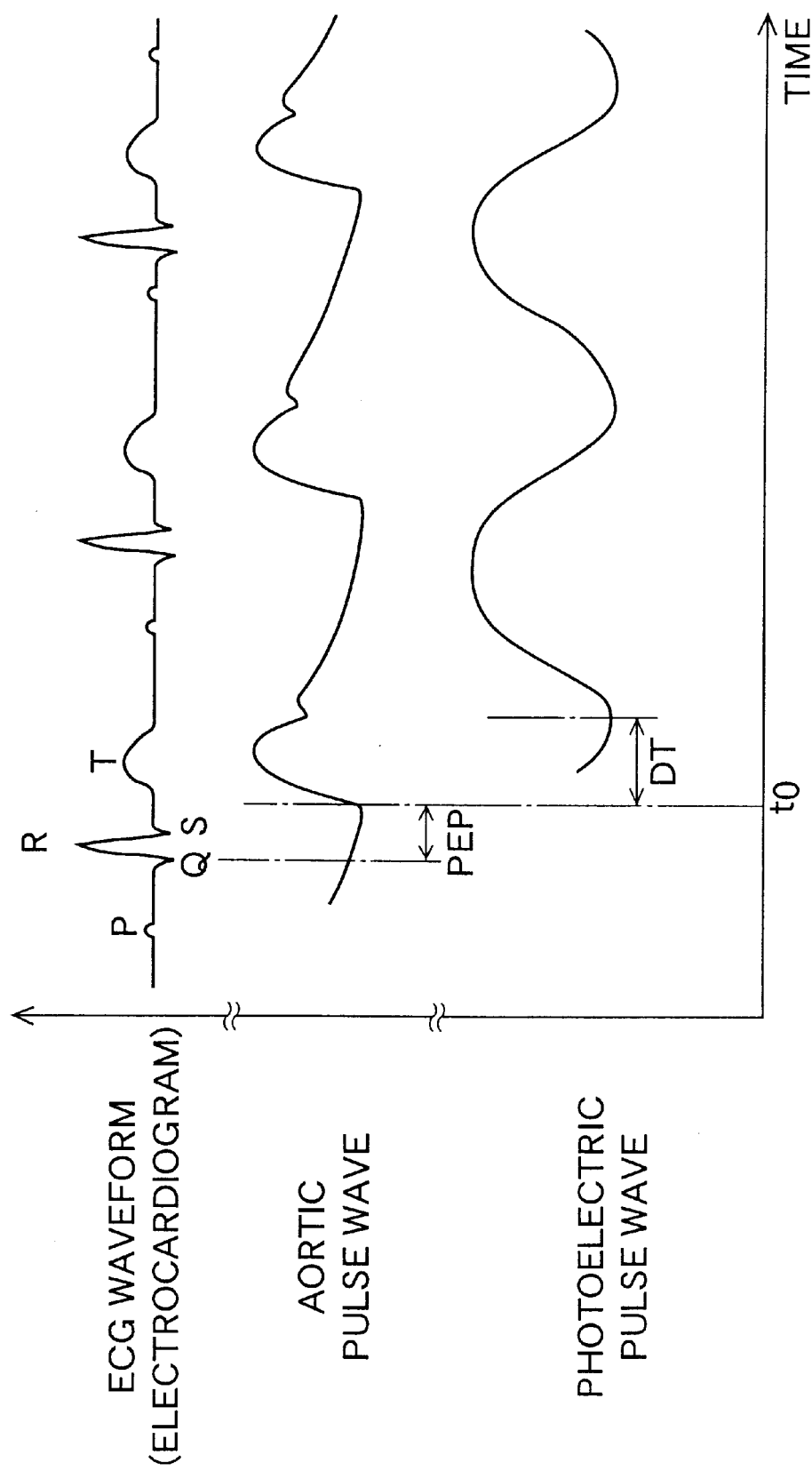

HEART-SOUND DETECTING APPARATUS, SYSTEM FOR MEASURING PRE-EJECTION PERIOD BY USING HEART-SOUND DETECTING APPARATUS, AND SYSTEM FOR OBTAINING PULSE-WAVE-PROPAGATION-VELOCITY-RELATING INFORMATION BY USING HEART-SOUND DETECTING APPARATUS

BACKGROUND OF THE INVENTION

1. Field of the Invention

The present invention relates to a heart-sound detecting apparatus which can determine a timing when aortic valve opens, a system for measuring a pre-ejection period by using a heart-sound detecting apparatus, and a system for obtaining information relating to a velocity at which a pulse wave propagates, by using a heart-sound detecting apparatus.

2. Related Art Statement

It is known that a first heart sound I, shown in FIG. 6A, has the following relationship with respective internal pressures of left ventricle, left atrium, and aorta of left half portion of the heart of a living person: When contraction of the ventricular muscle starts, the internal pressure of the left ventricle rapidly increases and, when the internal pressure of the left ventricle exceeds that of the left atrium, the mitral valve closes, which produces an initial portion of the first heart sound I. When the internal pressure of the left ventricle further increases and eventually exceeds that of the aorta, the aortic valve opens and ejection of blood starts so that blood flows from the left ventricle into the aorta. The opening of the aortic valve produces a remaining portion of the first heart sound I.

The sound produced by the opening of the aortic valve appears before the sound produced by the closing of the mitral valve disappears. Thus, in the first heart sound I, the sound resulting from the opening of the aortic valve overlaps the sound resulting from the closing of the mitral valve. In addition, the first heart sound I includes a sound resulting from the right half portion of the heart, such as a sound produced by the closing of the tricuspid valve that occurs substantially simultaneously with the closing of the mitral valve. Moreover, the first heart sound I includes internal noise produced in the body of the person. Thus, the first heart sound I is a complex sound and accordingly it has been difficult to determine, based on the first heart sound I, a timing when the aortic valve opens.

SUMMARY OF THE INVENTION

It is therefore an object of the present invention to provide a heart-sound detecting apparatus which can accurately determine a timing when aortic valve opens.

The above object has been achieved by the present invention. According to a first feature of the present invention, there is provided a heart-sound detecting apparatus, comprising a heart-sound microphone which detects at least one heart sound produced by a heart of a living subject and outputs a heart-sound signal representing the detected heart sound; a time-frequency analyzing means for analyzing, with respect to time and frequency, at least a portion of the heart-sound signal that includes a first heart sound I; and an aortic-valve-opening-timing determining means for determining a timing when an aortic valve of the heart opens, based on a time when a magnitude of the analyzed signal at a frequency higher than a frequency range of a main component present in an initial portion of the first heart-sound I is greater than a prescribed threshold value.

The sound resulting from the opening of the aortic valve follows the sound, resulting from the closing of the mitral valve and the tricuspid valve, as the main component present in the initial portion of the first heart sound I, and provides part of the remaining portion of the first heart sound I. Since the aortic-valve-opening-timing determining means determines a timing of opening of the aortic valve, based on a time when a magnitude of the analyzed signal at a frequency higher than a frequency range of the main component present in the initial portion of the first heart-sound I is greater than a prescribed threshold value, the determining means can accurately determine the timing.

According to a second feature of the present invention, there is provided a heart-sound detecting apparatus, comprising a heart-sound microphone which detects at least one heart sound produced by a heart of a living subject and outputs a heart-sound signal representing the detected heart sound; a time-frequency analyzing means for analyzing, with respect to time and frequency, at least a portion of the heart-sound signal that includes a first heart sound I; and an aortic-valve-opening-timing determining means for determining a timing when an aortic valve of the heart of the subject opens, based on a time when at least one magnitude of the analyzed signal at least one frequency in a frequency range of a main component present in an initial portion of the first heart-sound I is minimal.

The magnitude of the analyzed signal at a certain frequency in the frequency range of the main component present in the initial portion of the first heart-sound I first decreases, and then increases as the aortic valve opens. Since the aortic-valve-opening-timing determining means determines a timing of opening of the aortic valve, based on a time when at least one magnitude of the analyzed signal at least one frequency in the frequency range of the main component present in the initial portion of the first heart-sound I is minimal, the determining means can accurately determine the timing.

The heart-sound detecting apparatus according to the first or second feature may be employed as part of a pre-ejection-period measuring system. According to a third feature of the present invention, there is provided a system for measuring a pre-ejection period between a timing when contraction of a heart of a living subject starts and a timing when blood is ejected from the heart to an aorta of the subject, the system comprising an electrocardiograph for detecting an electrocardiogram from the subject; a heart-sound detecting apparatus according to the first or second feature; and a pre-ejection-period determining means for determining, as the pre-ejection period, a time difference between a timing when a portion of the electrocardiogram indicative of excitation of a ventricular muscle of the heart is detected by the electrocardiograph, and the timing of opening of the aortic valve determined by the aortic-valve-opening-timing determining means of the heart-sound detecting apparatus.

In the present system, the aortic-valve-opening-timing determining means of the heart-sound detecting apparatus accurately determines a timing of opening of the aortic valve, and the pre-ejection-period determining means determines, as the pre-ejection period, a time difference between a timing when a portion of the electrocardiogram indicative of the excitation of the ventricular muscle of the heart is detected, and the timing of opening of the aortic valve. Thus, an accurate pre-ejection period is determined.

The heart-sound detecting apparatus according to the first or second feature may be employed as part of a pulse-wavepropagation-velocity-relating-information obtaining system. According to a fourth feature of the present invention, there is provided a system for obtaining information relating to a propagation velocity at which a pulse wave propagates along an artery of a living subject, the system comprising a heart-sound detecting apparatus according to the first or second feature; a pulse-wave detecting device which is adapted to be worn on the subject to detect the pulse wave which propagates along the artery of the subject; and a pulse-wave-propagation-velocity-relating-information obtaining means for obtaining the information based on the timing of opening of the aortic valve determined by the aortic-valve-opening-timing determining means of the heart-sound detecting apparatus, and a timing when a rising point of the pulse wave is detected by the pulse-wave detecting device.

In the present system, the aortic-valve-opening-timing determining means of the heart-sound detecting apparatus accurately determines a timing of opening of the aortic valve, and the pulse-wave-propagation-velocity-relating-information obtaining means obtains pulse-wave-propagation-velocity-relating information based on the timing of opening of the aortic valve accurately determined by the aortic-valve-opening-timing determining means, and a timing when a rising point of the pulse wave is detected by the pulse-wave detecting device. Since a time difference between the timing of opening of the aortic valve and the timing of detection of the rising point of the pulse wave does not include a pre-ejection period, the time difference may be used as a sort of pulse-wave-propagation-velocity-relating information.

In a conventional method, pulse-wave-propagation-velocity-relating information is obtained by, e.g., using an electrocardiograph or a heart-sound microphone to detect an electrocardiogram or at least one heart sound as a heartbeat-synchronous pulse wave from an upstream-side portion of an artery. In this case, a time when a portion (e.g., Q-wave, R-wave, or S-wave) of the electrocardiogram signal that represents excitation of the ventricular muscle is detected, or a time when a first heart sound I starts, may be used as a first reference time. However, a time difference between the first reference time and a second reference time detected by a pulse-wave detecting device from a downstream-side portion of the artery includes a pre-ejection period PEP between the time when the excitation of the ventricular muscle starts and the time when blood is ejected into the aorta. Hence, it is needed to subtract the pre-ejection period PEP from the above-indicated time difference so as to calculate a pulse-wave propagation time DT needed for the pulse wave to propagation from the heart to the pulse-wave detecting device. Since, however, it is difficult to measure a pre-ejection period PEP, a prescribed value is used as the pre-ejection period PEP in many cases. However, the pre-ejection period PEP can change depending upon the condition of the heart, the conventional method cannot obtain sufficiently accurate pulse-wave-propagation-velocity-relating information. Since the pre-ejection period PEP is changed by, e.g., preload, the period PEP is used as an index to evaluate the cardiac function of a patient.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which:

FIG. 7 is a graph showing a manner in which a pre-ejection period PEP is determined by using a Q-wave as a waveform representing excitation of heart.

DETAILED DESCRIPTION OF PREFERRED EMBODIMENTS

Figure 1:
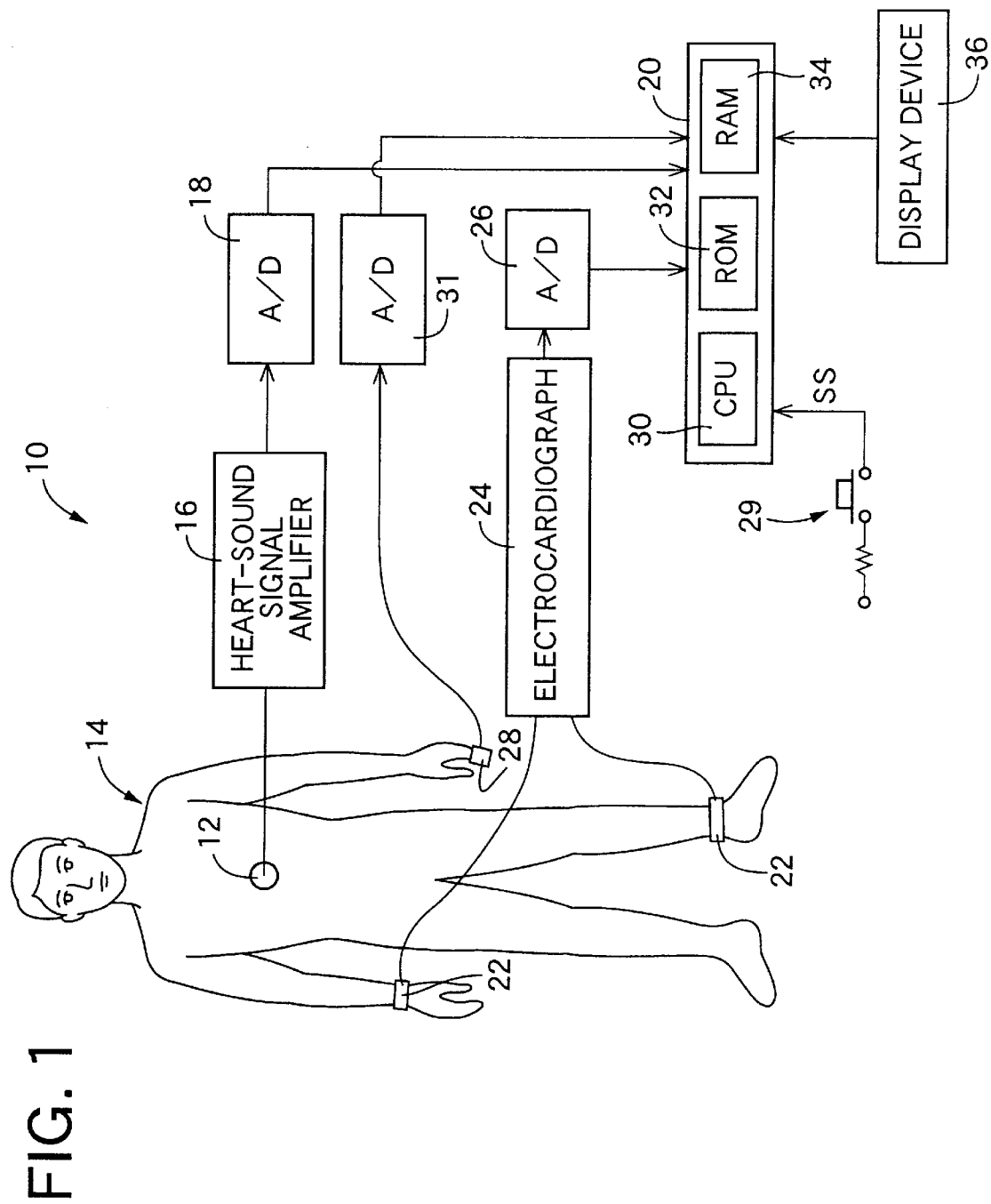
FIG. 1 is a diagrammatic view for explaining a construction of a pulse-wave-propagation-velocity-relating-information obtaining system which functions as a heart-sound detecting apparatus and a pre-ejection-period measuring apparatus, and to which the present invention is applied.

Hereinafter, there will be described an embodiment of the present invention, by reference to the drawings. FIG. 1 is a diagrammatic view for explaining. the construction of a pulse-wave-propagation-velocity-relating-information obtaining system 10 functioning as a heart-sound detecting apparatus and a pre-ejection-period measuring apparatus, to which the present invention is applied.

In FIG. 1, the present system 10 includes a heart-sound microphone 12 which is fixed, with an adhesive tape or the like, not shown, to a prescribed location on a chest of a living subject 14. The microphone 12 incorporates a piezoelectric element, not shown, which converts heart sounds produced from the heart of the subject 14, into an electric signal, i.e., heart-sound signal SH. A heart-sound signal amplifier 16 includes four sorts of filters, not shown, which cooperate with one another to attenuate a low-pitch component having a great energy and thereby amplifies and filters a high-pitch component of the heart-sound signal SH. The heart-sound signal SH amplified by the signal amplifier 16 is supplied to an electronic control device 20 via an analog-to-digital (A/D) converter 18.

An electrocardiograph 24 includes two electrodes 22 which are adapted to be worn on respective body portions of the subject 14 that are distant from each other via the heart, and which cooperate with each other to provide an electrocardiogram signal SE representing an action potential of the cardiac muscle of the subject 14. In the present embodiment, the two electrodes 22 are worn on a right wrist and a left ankle of the subject 14, respectively, to provide a two-electrode-induced electrocardiogram. The electrocardiogram signal SE produced by the electrodes 22 is amplified by an amplifier, not shown, of the electrocardiograph 24, and then is supplied to the control device 20 via an A/D converter 26.

A photoelectric-pulse-wave sensor 28 functions as a pulse-wave detecting device which detects a pulse wave propagated to peripheral arterioles including capillaries, and may have a construction similar to that of one which is used to detect pulse. The sensor 28 is worn on a body portion (e.g., a free end portion of a finger) of the subject 14. The sensor 28 includes a housing, not shown, which can accommodate a body portion of the subject 14; a light emitting element, not shown, as a light source which emits, toward a skin of the subject 14, a red or infrared light in such a wavelength band that can be reflected by hemoglobin, preferably a light having a wavelength of about 800 nm that is not influenced by blood oxygen saturation; and a light receiving element, not shown, which detects the light scattered from the body portion under the skin. The sensor 28 outputs a photoelectric-pulse-wave signal SM representing respective instantaneous volumes of the blood present in the capillaries of the body portion, and supplies the signal SM to the control device 20 via an A/D converter 30. The photoelectric-pulse-wave signal SM changes or pulsates in synchronism with each heartbeat of the subject 14, and represents the instantaneous amount of the hemoglobin present in the capillaries of the body portion under the skin, i.e., the volume of the blood present in the capillaries.

A push button 29 supplies, when being pushed by an operator, a start signal SS to the control device 20.

The control device 20 is essentially provided by a so-called microcomputer including a central processing unit (CPU) 30, a read only memory (ROM) 32, a random access memory (RAM) 34, an input-and-output (I/O) port, not shown, etc. The control device 20 or the CPU 30 processes signals according to control programs pre-stored in the ROM 32, while utilizing a temporary-storage function of the RAM 34. More specifically described, the control device 20 analyzes, with respect to time and frequency, a heart-sound waveform represented by the heart-sound signal SH, and thereby determines a timing when the aortic valve of the heart of the subject 14 opens; additionally, determines a pre-ejection period PEP based on the thus determined aortic-valve-opening timing and the electrocardiogram signal SE; obtains a piece of pulse-wave-propagation-velocity-relating information based on the thus determined aortic-valve-opening timing and the photoelectric-pulse-wave signal SM; and finally, operates a display device 36 to display the thus determined pre-ejection period PEP and the obtained pulse-wave-propagation-velocity-relating information.

Figure 2:
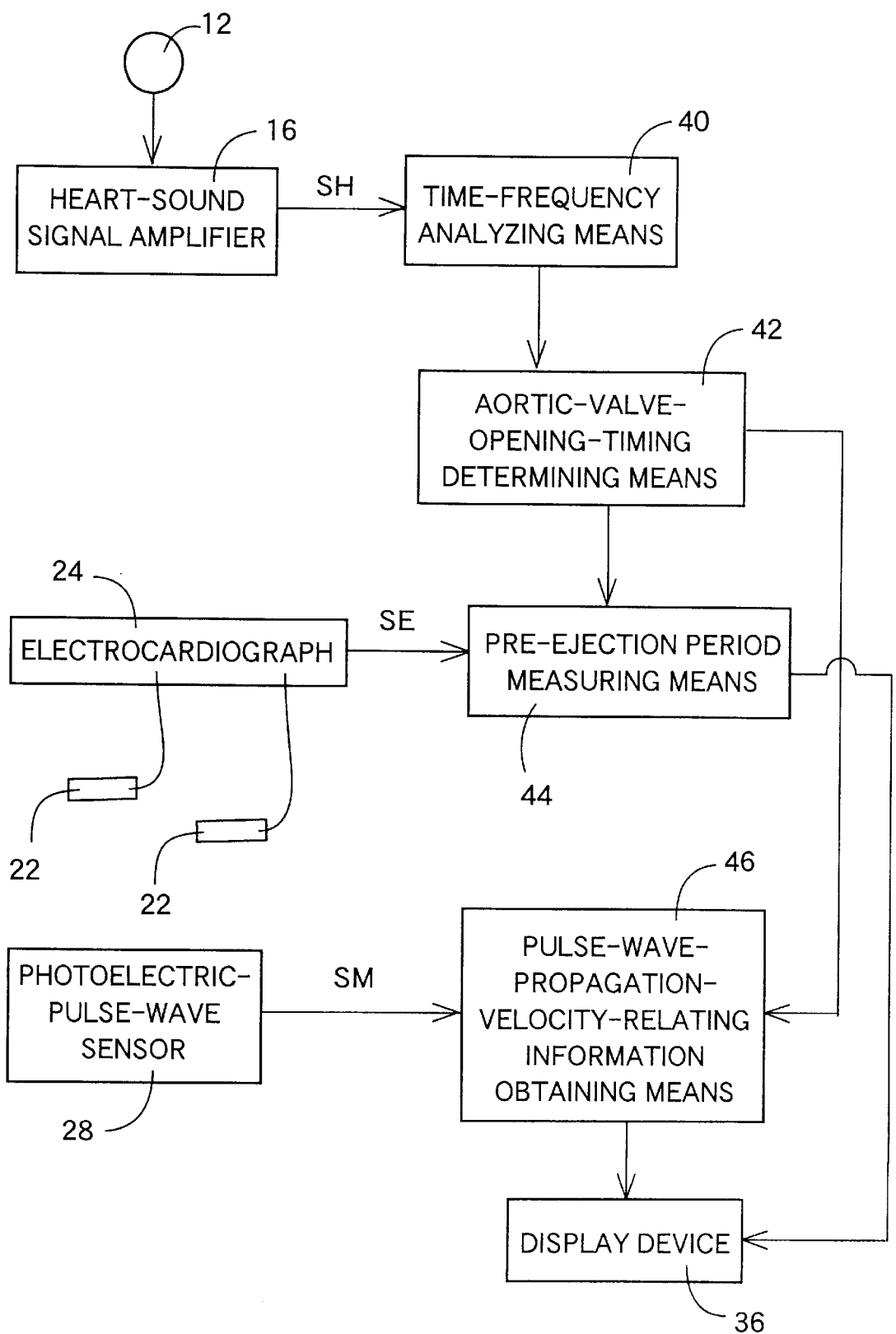
FIG. 2 is a block diagram for explaining essential functions of an electronic control device of the system of FIG. 1.

FIG. 2 is a block diagram for explaining essential functions of the control device 20 of the information obtaining system 10. In the figure, a time-frequency analyzing means 40 identifies, and cuts out, a portion of the heart-sound signal SH, supplied from the microphone 12, that represents a first heat sound I, and simultaneously analyzes, with respect to both time and frequency, the cut-out portion of the heart-sound signal SH. Thus, the time-frequency analyzing means 40 provides a time-wise change of the frequency-analyzed values of the signal SH, by utilizing, e.g., a wavelet transform, or a fast Fourier transform (FFT) as applied to each of prescribed time intervals.

Figure 3:
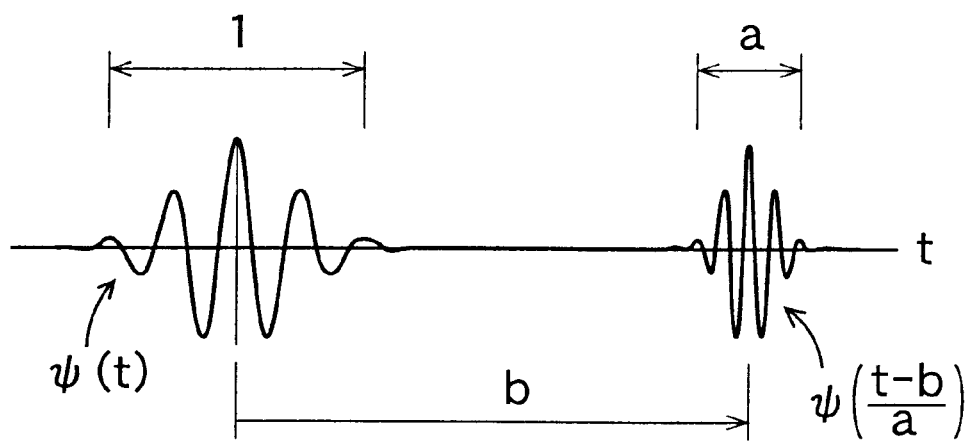
FIG. 3 is a graph showing a wavelet function.

The wavelet transform will be described below. A wavelet function, $\Psi(t)$, shown in FIG. 3, is modified to a function, $\Psi((t-b)/a)$, of a translate parameter, b, to translate a waveform represented by the function $\Psi(t)$, along a time axis, t, and a scale parameter, a, to expand or contract the width of the waveform represented by the function $\Psi(t)$, along the time axis t. The wavelet transform is defined as a function of the parameters a, b that is obtained by integrating, with respect to the time t, the product of the thus modified wavelet function $\Psi((t-b)/a)$ and a function f(t) representing the above-described cut-out heart-sound signal SH. That is, the wavelet transform is defined by the following expression (1) pre-stored in the ROM 32:

$$W(b, 1/a) = \int_{-\infty}^{\infty} \frac{1}{\sqrt{|a|}} \overline{\Psi\left(\frac{t-b}{a}\right)} f(t) dt \tag{1}$$

Since the waveform represented by the modified wavelet function $\Psi((t-b)/a)$ has a width scaled by the parameter a along the time axis t, a parameter, 1/a, indicates frequency; and since the waveform represented by the wavelet function $\Psi((t-b)/a)$ is translated by the parameter b along the time axis t, the parameter b indicates time.

Figure 4A:
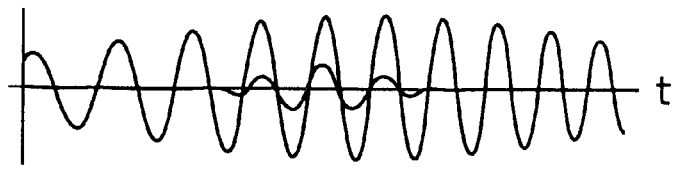
FIG. 4A is a graph showing a wavelet function $\Psi((t-b)/a)$ which approximates a portion of a certain function g(t)
Figure 4B:
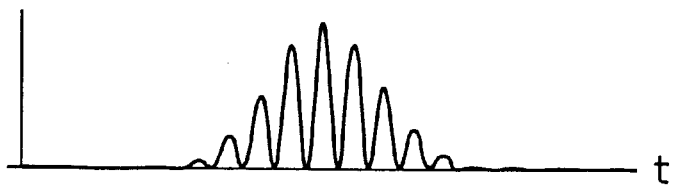
FIG. 4B is a graph showing the product of the wavelet function $\Psi((t-b)/a)$ and the function g(t)
Figure 5A:
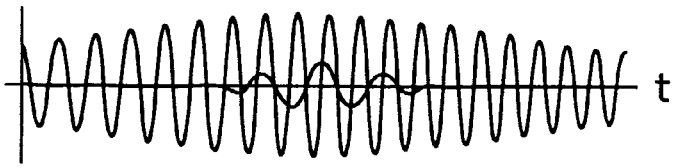
FIG. 5A is a graph showing the wavelet function $\Psi((t-b)/a)$ which does not approximates a portion of a certain function h(t)
Figure 5B:
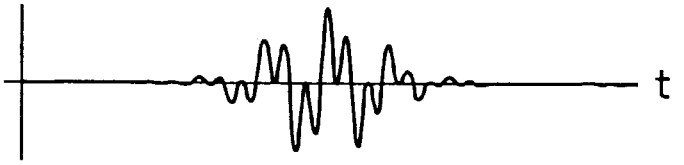
FIG. 5B is a graph showing the product of the wavelet function $\Psi((t-b)/a)$ and the function h(t)

FIGS. 4A and 4B, and FIG. 5A and 5B are graphs for explaining what is meant by the wavelet transform defined by the above expression (1). FIG. 4A shows that a wavelet function $\Psi((t-b)/a)$ in which appropriate parameters a, b have been selected substantially approximates a portion of a certain function g(t); and FIG. 5A shows that the wavelet function $\Psi((t-b)/a)$ does not approximates any portions of a certain function h(t). FIG. 4B shows the product of the wavelet function $\Psi((t-b)/a)$ and the function g(t) shown in FIG. 4A; and FIG. 5B shows the product of the wavelet function $\Psi((t-b)/a)$ and the function h(t) shown in FIG. 5A. In the case, shown in FIG. 4A, in which the wavelet function $\Psi((t-b)/a)$ substantially approximates a portion of the function g(t), the plus or minus sign of the product of the wavelet function $\Psi((t-b)/a)$ and the function g(t) does not change as the time t elapses. Therefore, a great value is obtained by integrating the product function. On the other hand, in the case, shown in FIG. 5A, in which the wavelet function $\Psi((t-b)/a)$ does not approximate any portions of the function h(t), the plus and minus sign of the product of the wavelet function $\Psi((t-b)/a)$ and the function h(t) frequently changes from plus to minus and from minus to plus as the time t elapses. Therefore, only a small value is obtained by integrating the product function. Thus, the above-indicated expression (1) provides a great value when the parameters a, b are appropriately selected so that the wavelet function $\Psi((t-b)/a)$ approximates a portion of the function f(t) representing the cut-out portion of the heart-sound signal SH; and the expression (1) provides a small value when the wavelet function $\Psi((t-b)/a)$ does not approximate any portions of the function f(t).

Figure 6A:
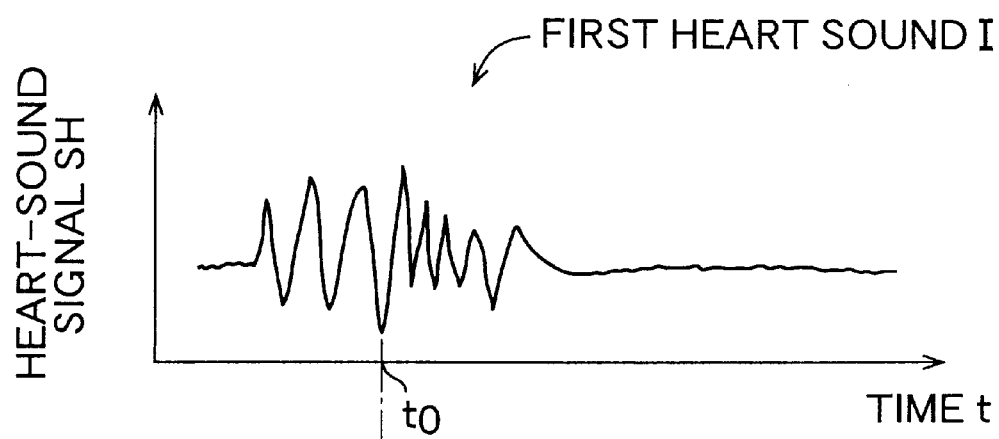
FIG. 6A is a graph showing a portion of a heart-sound signal SH that is cut out by a time-frequency analyzing means shown in FIG. 2.
Figure 6B:
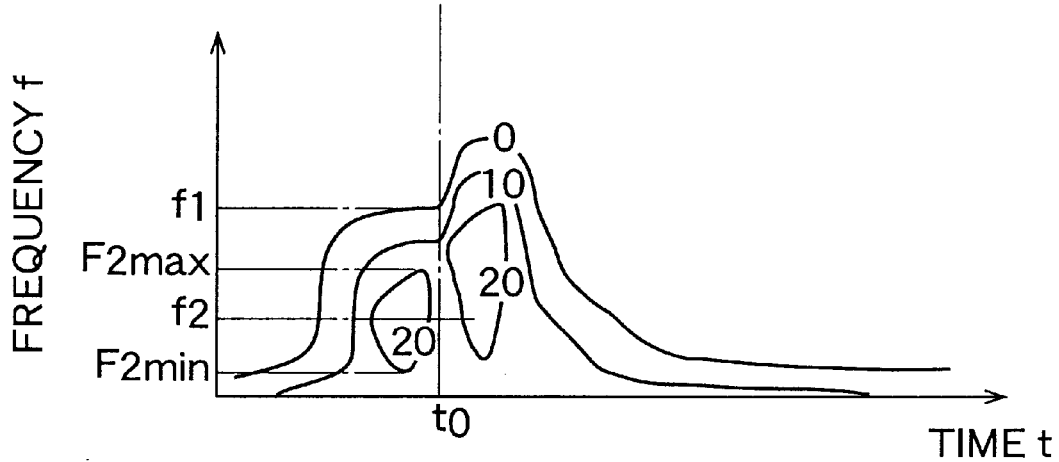
FIG. 6B is a graph showing a contour map which is obtained by subjecting the cut-out heart-sound signal SH shown in FIG. 6A, to a time-frequency analysis, i.e., a wavelet transform.

In the above-indicated expression (1), the scale parameter a corresponding to the frequency f and the translate parameter b corresponding to the time t are gradually changed and, each time at least one of the two parameters a, b is changed, an integral value is obtained from the wavelet transform, i.e., expression (1). FIG. 6A shows a waveform represented by the function f(s) representing the cut-out portion of the heart-sound signal SH; and FIG. 6B shows a three-dimensional graph (i.e., a contour map) that is obtained by analyzing the above waveform with respect to time, frequency, and signal magnitude by utilizing the expression (1). In the contour map, three contour lines represent three integral values, i.e., 0, 10, and 20, respectively.

The fast Fourier transform transforms a signal (i.e., a two-dimensional signal with respect to time and signal magnitude) that is obtained from each of prescribed time intervals, into a different sort of two-dimensional signal with respect to frequency and signal magnitude. Therefore, if the function f(t) is subjected to the fast Fourier transform each time the time t is moved from one time interval to the next time interval, the function f(t) is transformed into a three-dimensional signal with respect to time, frequency, and signal magnitude, like the contour map obtained by the wavelet transform.

An aortic-valve-closing-timing determining means 42 determines a timing when the aortic valve opens, based on a time-wise change of the values obtained by the time-frequency analyzing means 40 by analysis of the first heart sound I with respect to frequency, i.e., the values obtained by analysis of the first heart sound I with respect to time and frequency, for example, a time, $t_0$, when the magnitude of the analyzed first heart sound I at a first frequency, $f_1$, higher than a frequency range, RF, of a main component present in an initial portion of the first heart-sound I is greater than a prescribed threshold value, TH.

The first heart sound I starts when the mitral valve and the tricuspid valve close. Therefore, the initial portion of the first heart sound I includes, as its main component, the sound resulting from the closing of the mitral valve and the tricuspid valve, and does not include a sound resulting from opening of the aortic valve yet. The aortic valve opens when the isovolumetric systole terminates after the closing of the mitral valve and the tricuspid valve. The "initial portion" of the first heart sound I is defined as a prescribed period that occurs before the opening of the aortic valve and is shorter than the isovolumetric-systole period. The frequency range RF is defined by an upper-limit frequency $RF_{max}$ and a lower-limit frequency $RF_{min}$ that correspond to respective signal magnitudes that are greater than a prescribed reference value.

Experiments show that when the aortic valve opens, a high-frequency component which does not occur to the initial portion or period occurs to the first heart sound I. Therefore, the above-indicated first frequency $f_i$ may be determined as, e.g., a value obtained by adding a prescribed value to the upper-limit frequency $Rf_{max}$ of the frequency range RF of the main component present in the initial portion of the first heart sound I, or multiplying the upper-limit frequency $RF_{max}$ by a prescribed value greater than one. In this case, the determining means 42 determines the upper-limit frequency $RF_{max}$ (and the lower-limit frequency $RF_{min}$) of the frequency range RF, based on the contour map shown in FIG. 6B. Alternatively, it is possible to experimentally determine, in advance, a first frequency $f_1$ that is characteristic of the opening of aortic valve.

The threshold value TH is prescribed as a value which is as small as possible a value that is, however, greater than a signal magnitude of internal or external noise mixed with the first heart sound I.

FIG. 6B shows a timing, $t_0$, of opening of the aortic valve that is determined by the aortic-valve-closing-timing determining means 42, in the case where a first frequency f1 which is experimentally determined in advance is employed.

A pre-ejection-period determining means 44 determines, as a pre-ejection period PEP, a time difference between a timing when a portion (e.g., Q-wave, R-wave, or S-wave) of the electrocardiogram that indicates excitation of the ventricular muscle of the heart is detected by the electrocardiograph 24, and the timing of opening of the aortic valve determined by the aortic-valve-opening-timing determining means 42. The display device 36 displays the thus determined pre-ejection period PEP. FIG. 7 shows a manner in which a pre-ejection period PEP is determined by using R-wave as a waveform representing excitation of the ventricular muscle of the heart. In addition, FIG. 7 shows an aortic pulse wave, for easier understanding purposes only, that is not measured in the present embodiment.

A pulse-wave-propagation-velocity-relating-information obtaining means 46 includes a pulse-wave-propagation-time determining means which iteratively determines, as illustrated. in FIG. 7, a time difference between the timing of opening of the aortic valve, determined by the aortic-valve-opening-timing determining means 42, and a timing when a rising point of the photoelectric pulse wave is detected by the photoelectric-pulse-wave sensor 28, as a propagation time DT (second) which is needed for the pulse wave to propagate from the aortic valve to a position where the sensor 28 is worn on the subject 14. The information obtaining means 72 calculates, based on each of the pulse-wave propagation time values DT iteratively determined by the pulse-wave-propagation-time determining means, a pulse-wave propagation velocity PWV (m/sec) at which the pulse wave propagates along an artery of the subject 14, according to the following expression (2) pre-stored in the ROM 48:

$$PWV=L/DT \qquad (2)$$

where L (m) is a propagation distance from the initial portion of the aorta to the position where the sensor 28 is worn.

In the above expression (2), L is a constant which is experimentally determined in advance. The display device 52 displays each of the pulse-wave propagation velocity values PWV iteratively calculated by the information obtaining means 72. Since the timing to of opening of the aortic valve indicates a timing when blood is actually ejected into the aorta, an accurate pulse-wave propagation time DT that does not include a pre-ejection period PEP is obtained, and an accurate pulse-wave propagation velocity is calculated based on the accurate pulse-wave propagation time DT.

Figure 8:
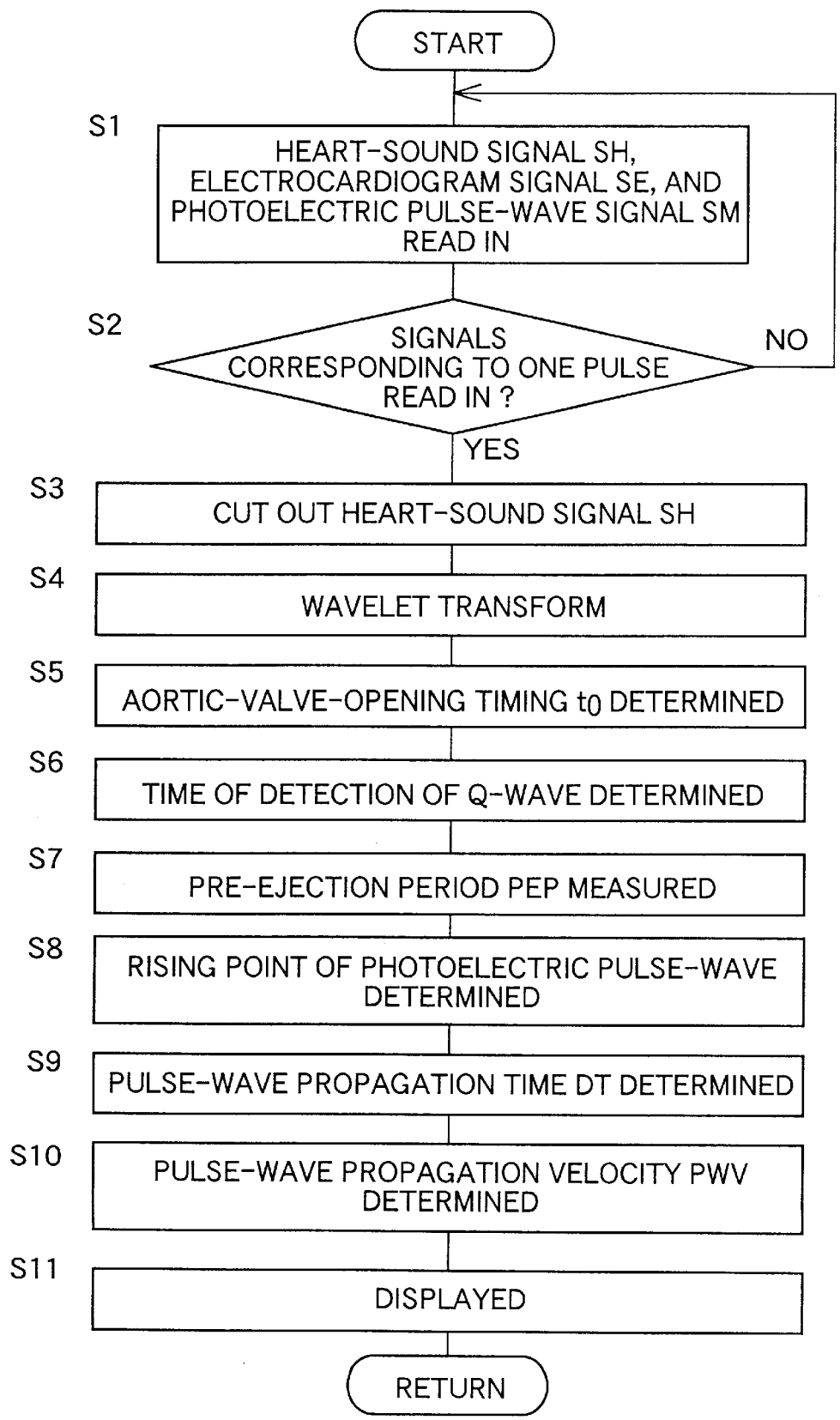
FIG. 8 is a flow chart representing a control program according to which the control device shown in FIG. 3 controls the system of FIG. 1.

FIG. 8 is a flow chart for explaining the essential functions of the control device 20, illustrated in the block diagram of FIG. 2. A control routine according to this flow chart is started when the push button 29 is pushed and a start signal SS is supplied from the button 29 to the control device 20.

In FIG. 6, at Step S1 (hereinafter, Step is omitted), the control device 20 reads in the heart-sound signal SH supplied from the microphone 12, the electrocardiogram signal SE supplied from the electrocardiograph 24, and the photoelectric-pulse-wave signal SM supplied from the photoelectric-pulse-wave sensor 28.

Subsequently, at S2, the control device 20 judges, based on whether the device 20 has read in a rising point of the signal SM, whether the device 20 has read in, at S1, respective lengths of the three signals SH, SE, SM that correspond to one-time heartbeat of the subject 14. If a negative judgment is made at S2, S1 is repeated to continue reading in the three signals SH, SE, SM.

On the other hand, if a positive judgment is made at S2, the control of the control device 20 proceeds with S3 and S4 corresponding to the time-frequency analyzing means 40. First, at S3, the control device 20 cuts out a portion of the heart-sound signal SH that surely includes a first heart sound I, e.g., has a length corresponding to 150 msec as measured from a time when the preceding rising of the pulse-wave signal SM was detected. Then, at S4, the heart-sound signal SH cut out at S3 is subjected to time-frequency analysis using the wavelet transform.

Subsequently, at S5 corresponding to the aortic-valve-opening-timing determining means 42, the control device 20 determines, as a timing of opening of the aortic valve, a time $t_0$ when the magnitude of the analyzed signal at a prescribed first frequency $f_1$ characteristic of opening of aortic valve, first exceeds a prescribed threshold value TH.

Then, at S6, the control device 20 determines, based on the electrocardiogram signal SE read in at S1, a time when a Q-wave is detected by the electrocardiograph 24. In addition, at S7 corresponding to the pre-ejection-period measuring means 44, the control device 20 determines, as a pre-ejection period PEP, a time difference between the time of detection of the Q-wave determined at S6, and the timing $t_0$ of opening of the aortic valve determined at S5.

Subsequently, at S8, the control device 20 determines, based on the pulse-wave signal SM read in at S1, a timing when the current ring point of the signal SM is detected by the pulse-wave sensor 28. Then, the control of the control device 20 goes to S9 and S10 corresponding to the pulse-wave-propagation-velocity-relating-information obtaining means 46. First, at S9, the control device 20 determines, as a pulse-wave propagation time DT, a time difference between the timing to of opening of the aortic valve determined at S5 and the timing of detection of the rising point of the photoelectric pulse wave determined at S8. S9 is followed by S10 where the control device 20 replaces the variable DT of the expression (2), with the pulse-wave propagation time DT determined at S9, and thereby calculates a pulse-wave propagation velocity PWV.

S10 is followed by S11 where the control device 20 operates the display device 52 to display the pre-ejection period PEP determined at S7 and the pulse-wave propagation velocity PWV calculated at S10. Then, S1 and the following steps are repeated, while a timing of opening of the aortic valve is iteratively determined, and a pulse-wave propagation velocity PWV is iteratively calculated based on each of the iteratively determined timings of opening of the aortic valve, in synchronism with each heartbeat of the subject.

It clearly emerges from the foregoing description of the present embodiment that the aortic-valve-opening-timing determining means 42 (S5) determines, as a timing of opening to of the aortic valve, a time when the magnitude of the analyzed signal at the first frequency f1 higher than the frequency range RF first exceeds the prescribed threshold value TH. The analyzed signal is obtained by the time-frequency analyzing means 40 (S3 and S4), i.e., by subjecting the heart-sound signal SH to the time-frequency analysis, i.e., the wavelet transform. Therefore, the aortic-valve-opening-timing determining means 42 can accurately determine the timing $t_0$ of opening of the aortic valve.

In addition, in the present embodiment, the aortic-valve-opening-timing determining means 42 (S5) accurately determines the timing $t_0$ of opening of the aortic valve, and the pre-ejection-period determining means 44 (S7) determines, as a pre-ejection period PEP, a time difference between a timing when a Q-wave of the electrocardiogram is detected by the electrocardiograph 24 and the timing $t_0$ of opening of the aortic valve determined by the determining means 42 (S5). Thus, the pre-ejection-period determining means 44 (S7) can accurately determine the pre-ejection period PEP.

Moreover, in the present embodiment, the aortic-valve-opening-timing determining means 42 (S5) accurately determines the timing $t_0$ of opening of the aortic valve, and the pulse-wave-propagation-velocity-relating-information obtaining means 46 (S9 and S10) determines a pulse-wave propagation velocity PWV based on a pulse-wave propagation time DT, i.e., a time difference between the accurately determined timing $t_0$ of opening of the aortic valve and the timing when the rising point of the photoelectric pulse wave is detected by the photoelectric-pulse-wave sensor 28. Since the time difference between the timing $t_0$ of opening of the aortic valve and the timing of detection of the rising point of the photoelectric pulse wave does not include the pre-ejection period PEP. Therefore, the thus determined pulse-wave propagation time DT and pulse-wave propagation velocity PWV are accurate.

While the present invention has been described in detail in its preferred embodiment, by reference to the drawings, the invention may otherwise be embodied.

For example, the aortic-valve-opening-timing determining means 42 may be modified to determine a timing of opening of the aortic valve based on a time when at least one magnitude of the analyzed signal at least one frequency in the frequency range RF of the main component present in the initial portion of the first heart-sound I is minimal. The analyzed signal is obtained by the time-frequency analyzing means 40, i.e., by subjecting the heart-sound signal SH to the time-frequency analysis. As described previously, the main component of the initial portion of the first heart sound I results from the closing of the mitral valve and the tricuspid valve. Therefore, after the closing of those valves ends, respective magnitudes of the analyzed signal at respective frequencies in the frequency range RF decrease. However, thereafter, when the aortic valve opens, the respective magnitudes of the analyzed signal at the respective frequencies in the frequency range RF increase. Thus, it is possible to determine a timing of opening of the aortic valve based on a time when at least one magnitude of the analyzed signal at least one frequency in the frequency range RF takes a minimal value. For example, it is possible to determine a timing $t_0$ of opening of the aortic valve, based on a time when an average of respective magnitudes of the analyzed signal at two or more frequencies in a prescribed portion, or an entirety, of the frequency range RF is minimal. Alternatively, it is possible to determine a timing $t_0$ of opening of the aortic valve, based on a time when a magnitude of the analyzed signal at a single frequency (shown as second frequency $f_2$ in the graph of FIG. 6B) in the frequency range RF is minimal. In the example shown in FIG. 6B, the second frequency $f_2$ is equal to an average of an upper-limit frequency $F_{2max}$ and a lower-limit frequency $F_{2min}$ of the frequency range RF. It is found that the respective timings of opening of the aortic valve determined using the first frequency $f_1$ and the second frequency $f_2$ are substantially equal to each other.

Moreover, it is possible to determine a timing $t_0$ of opening of the aortic valve, based on both a first time when a magnitude of the analyzed signal at a frequency higher than the frequency range RF is greater than a threshold value TH and a second time when at least one magnitude of the analyzed signal at least one frequency in the frequency range RF is minimal, for example, determine an average of the first and second times. as the timing $t_0$.

In addition, in the illustrated embodiment, the photoelectric-pulse-wave sensor 28 which is worn on an end portion of a finger of the subject 14 is employed as a pulse-wave detecting device. However, a pressure-pulse-wave sensor which is pressed against a prescribed portion of a living subject and detects a pressure pulse wave propagated to the body portion, a pressure-pulse-wave sensor which includes a pressing band adapted to be worn on a prescribed portion (e.g., upper arm) of a living subject and detects a change of a pressure in the pressing band, a photoelectric-pulse-wave detecting probe for use with an oximeter, or an impedance-pulse-wave detecting device which detects an impedance change through electrodes worn on a finger of a living subject may be employed as the pulse-wave detecting device.

In the illustrated embodiment, the pulse-wave-propagation-velocity-relating-information obtaining means 46 (S9) determines, as a pulse-wave propagation time DT, a time difference between the timing $t_0$ of opening of the aortic valve and the time of detection of rising point of the photoelectric pulse wave. However, it is possible to determine a time difference between a time when an electrocardiographic wave (e.g., Q-wave, R-wave, or S-wave) representing excitation of the ventricular muscle is detected by the electrocardiograph 24, and the time of detection of rising point of the photoelectric pulse wave, and determine a pulse-wave propagation time DT by subtracting, from the thus determined time difference, the pre-ejection period PET determined by the pre-ejection-period determining means 44 (S7).

In the illustrated embodiment, the time-frequency analyzing means 40 (S3 and S4) cuts out a portion of the heart-sound signal SH that includes the first heart sound I, and subjects only the cut out portion of the signal SH to the time-frequency analysis. However, the time-frequency analyzing means 40 (S3 and S4) may be modified to subject the entirety of the heart-sound signal SH supplied from the microphone 12, to the time-frequency analysis.

In the illustrated embodiment, the pulse-wave-propagation-velocity-relating-information obtaining system 10 employs the pre-ejection-period measuring or determining means 44 (S7) which measures or determines the pre-ejection period PEP. However, it is possible to omit the pre-ejection-period determining means 44 (S7).

In the illustrated embodiment, the pulse-wave-propagation-velocity-relating-information obtaining system 10 may not employ the pulse-wave-propagation-velocity-relating-information obtaining means 46 (S9 and S10). In this case, the system 10 may be called as a pre-ejection-period measuring system.

It is to be understood that the present invention may be embodied with other changes, improvements and modifications that may occur to a person skilled in the art without departing from the spirit and scope of the invention.

What is claimed is:

1. A heart-sound detecting apparatus, comprising:
    a heart-sound microphone which detects at least one heart sound produced by a heart of a living subject and outputs a heart-sound signal representing the detected heart sound;
    a time-frequency analyzing means for analyzing, with respect to time and frequency, at least a portion of the heart-sound signal that includes a first heart sound I; and
    an aortic-valve-opening-timing determining means for determining a timing when an aortic valve of the heart opens, based on a time when a magnitude of the analyzed signal at a frequency higher than a frequency range of a main component present in an initial portion of the first heart-sound I is greater than a prescribed threshold value.

2. A heart-sound detecting apparatus, comprising:
    a heart-sound microphone which detects at least one heart sound produced by a heart of a living subject and outputs a heart-sound signal representing the detected heart sound;
    a time-frequency analyzing means for analyzing, with respect to time and frequency, at least a portion of the heart-sound signal that includes a first heart sound I; and
    an aortic-valve-opening-timing determining means for determining a timing when an aortic valve of the heart of the subject opens, based on a time when at least one magnitude of the analyzed signal at least one frequency in a frequency range of a main component present in an initial portion of the first heart-sound I is minimal.

3. A system for measuring a pre-ejection period between a timing when contraction of a heart of a living subject starts and a timing when blood is ejected from the heart to an aorta of the subject, the system comprising:
    an electrocardiograph for detecting an electrocardiogram from the subject;
    a heart-sound detecting apparatus according to claim 1; and
    a pre-ejection-period determining means for determining, as the pre-ejection period, a time difference between a timing when a portion of the electrocardiogram indicative of excitation of a ventricular muscle of the heart is detected by the electrocardiograph, and the timing of opening of the aortic valve determined by the aortic-valve-opening-timing determining means of the heart-sound detecting apparatus.

4. A system for measuring a pre-ejection period between a timing when contraction of a heart of a living subject starts and a timing when blood is ejected from the heart to an aorta of the subject, the system comprising:
    an electrocardiograph for detecting an electrocardiogram from the subject;
    a heart-sound detecting apparatus according to claim 2; and
    a pre-ejection-period determining means for determining, as the pre-ejection period, a time difference between a timing when a portion of the electrocardiogram indicative of excitation of a ventricular muscle of the heart is detected by the electrocardiograph, and the timing of opening of the aortic valve determined by the aortic-valve-opening-timing determining means of the heart-sound detecting apparatus.

5. A system for obtaining information relating to a propagation velocity at which a pulse wave propagates along an artery of a living subject,-the system comprising:
    a heart-sound detecting apparatus according to claim 1;
    a pulse-wave detecting device which is adapted to be worn on the subject to detect the pulse wave which propagates along the artery of the subject; and
    a pulse-wave-propagation-velocity-relating-information obtaining means for obtaining said information based on the timing of opening of the aortic valve determined by the aortic-valve-opening-timing determining means of the heart-sound detecting apparatus, and a timing when a rising point of the pulse wave is detected by the pulse-wave detecting device.

6. A system according to claim 5, wherein the pulse-wave-propagation-velocity-relating-information obtaining means comprises a pulse-wave-propagation-time determining means for determining, based on the timing of opening of the aortic valve determined by the aortic-valve-opening-timing determining means, and the timing when the rising point of the pulse wave is detected by the pulse-wave detecting device, a propagation time needed for the pulse wave to propagate from the aorta to a position where the pulse-wave detecting device is worn on the subject.

7. A system according to claim 5, wherein the pulse-wave-propagation-velocity-relating-information obtaining means comprises a pulse-wave-propagation-velocity determining means for determining the propagation velocity at which the pulse wave propagates, by dividing a distance from the aorta to a position where the pulse-wave detecting device is worn on the subject, by a time difference between the timing of opening of the aortic valve determined by the aortic-valve-opening-timing determining means and the timing when the rising point of the pulse wave is detected by the pulse-wave detecting device.

8. A system according to claim 5, further comprising an output device which outputs the information obtained by the pulse-wave-propagation-velocity-relating-information obtaining means, so that an observer can observe said information.

9. A system for obtaining information relating to a propagation velocity at which a pulse wave propagates along an artery of a living subject, the system comprising:

a heart-sound detecting apparatus according to claim 2;

a pulse-wave detecting device which is adapted to be worn on the subject to detect the pulse wave which propagates along the artery of the subject; and a pulse-wave-propagation-velocity-relating-information obtaining means for obtaining said information based on the timing of opening of the aortic valve determined by the aortic-valve-opening-timing determining means of the heart-sound detecting apparatus, and a timing when a rising point of the pulse wave is detected by the pulse-wave detecting device.

10. A system according to claim 9, wherein the pulse-wave-propagation-velocity-relating-information obtaining means comprises a pulse-wave-propagation-time determining means for determining, based on the timing of opening of the aortic valve determined by the aortic-valve-opening-timing determining means, and the timing when the rising point of the pulse wave is detected by the pulse-wave detecting device, a propagation time needed for the pulse wave to propagate from the aorta to a position where the pulse-wave detecting device is worn on the subject.

11. A system according to claim 9, wherein the pulse-wave-propagation-velocity-relating-information obtaining means comprises a pulse-wave-propagation-velocity determining means for determining the propagation velocity at which the pulse wave propagates, by dividing a distance from the aorta to a position where the pulse-wave detecting device is worn on the subject, by a time difference between the timing of opening of the aortic valve determined by the aortic-valve-opening-timing determining means and the timing when the rising point of the pulse wave is detected by the pulse-wave detecting device.

12. A system according to claim 9, further comprising an output device which outputs the information obtained by the pulse-wave-propagation-velocity-relating-information obtaining means, so that an observer can observe said information.

* * * * *